US009061087B2

(12) United States Patent
Roberts et al.

(10) Patent No.: US 9,061,087 B2
(45) Date of Patent: Jun. 23, 2015

(54) METHOD OF MAKING A HEMOSTATIC SPONGE WOUND DRESSING COMPRISING SUBJECTING THE SPONGE TO WATER VAPOR

(75) Inventors: Keith A. Roberts, White Bear Lake, MN (US); Majid Zia, White Bear Township, MN (US)

(73) Assignee: Hemostasis, LLC, St. Paul, MN (US)

( * ) Notice: Subject to any disclaimer, the term of this patent is extended or adjusted under 35 U.S.C. 154(b) by 660 days.

(21) Appl. No.: 12/390,947

(22) Filed: Feb. 23, 2009

(65) Prior Publication Data

US 2009/0226391 A1 Sep. 10, 2009

Related U.S. Application Data

(60) Provisional application No. 61/068,226, filed on Mar. 4, 2008.

(51) Int. Cl.

| | |
|---|---|
| ***A61K 31/722*** | (2006.01) |
| ***A61K 31/715*** | (2006.01) |
| ***A61L 15/28*** | (2006.01) |
| ***A61L 15/42*** | (2006.01) |
| ***A61F 13/00*** | (2006.01) |
| ***A61K 9/70*** | (2006.01) |

(52) U.S. Cl.

CPC ......... *A61L 15/425* (2013.01); *A61F 13/00034* (2013.01); *A61K 9/7007* (2013.01); *A61K 31/722* (2013.01); *A61L 15/28* (2013.01); *A61L 2400/04* (2013.01)

(58) Field of Classification Search

None

See application file for complete search history.

(56) References Cited

U.S. PATENT DOCUMENTS

| | | | | |
|---|---|---|---|---|
| 2,423,475 | A | 7/1947 | Bice et al. | 128/270 |
| 2,465,357 | A | 3/1949 | Correll | 106/122 |
| 2,507,244 | A | 5/1950 | Correll | 260/117 |
| 2,558,395 | A | 6/1951 | Studer | 424/423 |
| 2,602,042 | A | 7/1952 | Abbott | 167/84 |
| 3,005,457 | A | 10/1961 | Millman | 128/296 |
| 3,122,479 | A | 2/1964 | Smith | 167/84 |
| 3,208,994 | A | 9/1965 | Flodin | 260/209 |
| 3,810,473 | A | 5/1974 | Cruz, Jr. et al. | 128/334 |
| 3,813,466 | A | 5/1974 | Anderson | 424/28 |
| 4,002,173 | A | 1/1977 | Manning et al. | 128/296 |
| 4,124,705 | A | 11/1978 | Rothman et al. | 424/180 |
| 4,126,669 | A | 11/1978 | Rothman et al. | 424/1 |
| 4,215,200 | A | 7/1980 | Miyata et al. | 435/273 |
| 4,225,580 | A | 9/1980 | Rothman et al. | 424/78 |
| 4,292,972 | A | 10/1981 | Pawelchak et al. | 128/296 |
| 4,394,373 | A | 7/1983 | Malette et al. | 424/95 |

(Continued)

FOREIGN PATENT DOCUMENTS

WO WO 2008/150246 A1 12/2008 ........... A61K 36/185

OTHER PUBLICATIONS

Ito, A. et al. Die Angewandte Makromolekulare Chemie (1997), 248; pp. 85-94.*

(Continued)

*Primary Examiner* — Kevin S Orwig

(74) *Attorney, Agent, or Firm* — Baker Botts L.L.P.

(57) ABSTRACT

A method of making a wound dressing comprises dissolving at least one hemostatic agent in at least one solvent to form a solution. The method continues by freeze drying the solution to form a sponge. The method further comprises compressing the sponge, wherein the sponge is subjected to a vapor above ambient temperature prior to or during the compression.

13 Claims, 3 Drawing Sheets

10
16
18
12
14

(56) References Cited

U.S. PATENT DOCUMENTS

| | | | | |
|---|---|---|---|---|
| 4,439,420 | A | 3/1984 | Mattei et al. | 424/78 |
| 4,537,767 | A | 8/1985 | Rothman et al. | 424/78 |
| 4,640,834 | A * | 2/1987 | Eibl et al. | 424/176.1 |
| 4,822,349 | A | 4/1989 | Hursey et al. | 604/367 |
| 5,206,028 | A * | 4/1993 | Li | 424/484 |
| 5,409,703 | A | 4/1995 | McAnalley et al. | 424/435 |
| 5,585,007 | A | 12/1996 | Antanavich et al. | 210/782 |
| 5,707,972 | A | 1/1998 | Shimizu | 514/54 |
| 5,770,705 | A | 6/1998 | Shanbrom | |
| 5,836,970 | A | 11/1998 | Pandit | 606/213 |
| 5,840,777 | A | 11/1998 | Eagles et al. | 521/82 |
| 5,851,461 | A | 12/1998 | Bakis et al. | 264/50 |
| 6,060,461 | A | 5/2000 | Drake | 514/54 |
| 6,638,918 | B2 * | 10/2003 | Davison et al. | 514/55 |
| 6,992,233 | B2 | 1/2006 | Drake | 602/48 |
| 7,070,722 | B1 | 7/2006 | Gilchrist et al. | 264/50 |
| 7,101,862 | B2 | 9/2006 | Cochrum et al. | 514/54 |
| 7,371,403 | B2 | 5/2008 | McCarthy et al. | 424/445 |
| 2002/0131933 | A1 * | 9/2002 | Delmotte | 424/1.11 |
| 2003/0073663 | A1 | 4/2003 | Wiseman et al. | 514/54 |
| 2004/0243043 | A1 | 12/2004 | McCarthy et al. | 602/46 |
| 2005/0038369 | A1 | 2/2005 | Gregory et al. | 602/48 |
| 2005/0137512 | A1 | 6/2005 | Campbell et al. | 602/41 |
| 2005/0147656 | A1 | 7/2005 | McCarthy et al. | 424/445 |
| 2006/0172000 | A1 * | 8/2006 | Cullen et al. | 424/445 |
| 2007/0066924 | A1 | 3/2007 | Hopman et al. | 602/48 |
| 2007/0082023 | A1 | 4/2007 | Hopman et al. | 424/426 |
| 2007/0148215 | A1 | 6/2007 | Teslenko et al. | 424/445 |
| 2009/0062233 | A1 | 3/2009 | Ji et al. | 514/60 |
| 2010/0291055 | A1 | 11/2010 | Athanasiadis et al. | 424/94.1 |

OTHER PUBLICATIONS

Mi, F.-L., et al. Biomaterials. (2001); 22; pp. 165-173.*

Ritthidej, G. C., et al. Int. J. Pharm. (2002), 232; pp. 11-22.*

Bhaskara Jasti, et al.; Business Briefing: Pharmatech; *Drug Delivery Polymers: Recent Advances in Mucoadhesive Drug Delivery Systems*; 3 pages, 2003.

Eric M. Acheson, et al.; The Journal of TRAUMA ® Injury, Infection, and Critical Care; *Comparison of Hemorrhage Control Agents Applied to Lethal Extremity Arterial Hemorrhages in Swine*; vol. 59, No. 4; pp. 865-875, Oct. 2005.

Roberts, et al., *Hemostat Agent and Method*, U.S. Appl. No. 11/861,719, filed Sep. 26, 2007 (US 2008-0076722).

International Search Report, mailing date Feb. 15, 2008, for International Application No. PCT/TR2007/00129, filed Feb. 4, 2008 (3 pgs).

USPTO; Office Action; U.S. Appl. No. 11/861,719, filed Sep. 26, 2007, in the name of Roberts, ( 25 pg; ), Notification Date Feb. 15, 2011.

Mitolo, J.J. (2006) "Starch Selection and Interaction in Foods" in Ingredient Interactions: Effects on Food Quality, 2nd Ed., Edited by Andrew McPherson and Anikumar G. Gaonkar, published by CRC Press, p. 139-166, release date: Dec. 2005.

Food Industries Manual (1997), edited by M.D. Ranke, R.c. Kill and C. Baker, Published by Blackie Academic and Professional, London, UK, pp. 488-489 (4 pgs total).

Keith A. Roberts, *Hemostatic Sponge with Enzyme and Method of Manufacture*, U.S. Appl. No. 61/238,754, filed Sep. 1, 2009.

USPTO; Office Action; U.S. Appl. No. 11/861,719, filed Sep. 26, 2007, in the name of Roberts, ( 9 pg; ), Notification Date Jun. 21, 2010.

Keith A. Roberts, *Hemostatic Sponge with Enzyme and Method of Manufacture*, U.S. Appl. No. 12/853,083, filed Aug. 9, 2010 (28 pgs.).

USPTO; Office Action; U.S. Appl. No. 11/861,719, filed Sep. 26, 2007, in the name of Roberts, ( 15 pg; ), Notification Date Sep. 9, 2010.

Murat, F.-J.L., Ereth, M.H., Dong, Y., Piedra, M.P., Gettman, M.T. (2004) Evaluation of Microporous Polysaccharide Hemospheres as a Novel Hemostatic Agent in Open Partial Nephrectomy: Favorable Experimental Results in the Porcine Model; the Journal of Urology, vol. 172, p. 1119-1122 (4 pg), Sep. 2004.

Niba, L.L "Carbohydrates: Starch" in Handbook of Food Science, Technology, and Engineering; vol. 1; edited by Y.H. Hui, published by CRC Press Taylor & Francis; p. 3-1 to 3-17; (17 pg), Dec. 19, 2005.

"Vitamin K" from the Vitamin & Herb University [on line]; [Retrieved on Sep. 4, 2010]; Retrieved from the internet at http://www.vitaminherbuniversity.com/topic.asp?categoryid=1&topicid=1011, published Sep. 25, 2003 (6 pg).

PCT, Notification of Transmittal of the International Search Report and the Written Opinion of the International Searching Authority, or the Declaration, International Application No. PCT/US2009/035386, Int'l fiing date Feb. 27, 2009, and PCT International Search Report, 13 pgs, Date Mailed May 31, 2010.

USPTO; Non-Final Office Action; U.S. Appl. No. 12/853,083, filed Aug. 9, 2010; in the name of Keith A. Roberts , (26 pgs), Notification Date Mar. 24, 2011.

USPTO; Final Office Action; U.S. Appl. No. 11/861,719, filed Sep. 26, 2007 ; in the name of Roberts; (32 pgs), Notification Date Jul. 12, 2011.

Roberts et al., U.S. Appl. No. 11/861,719, "Response Pursuant to 37 C.F.R. §1.111", (11 pgs.), Notification Date Jun. 1, 2011.

Roberts et al., U.S. Appl. No. 11/861,719, "Response Pursuant to 37 C.F.R. §1.114", (33 pgs.), Notification Date Nov. 3, 2011.

Roberts et al., U.S. Appl. No. 12/853,083, "Response Pursuant to 37 C.F.R. §1.111", (16 pgs.), Notification Date Jun. 20, 2011.

USPTO; Final Office Action; U.S. Appl. No. 12/853,083, filed Aug. 9, 2010; Keith A. Roberts , (34 pgs), Notification Date Aug. 12, 2011.

Park, S.-1., et al. , Functional Properties of Antimicrobial Lysozyme—Chitosan Composite Films, 2004 Institute of Food Technologists, vol. 69, Nr. 8, 2004, Journal of Food Science, Published on Web Sep. 29, 2004; pp. M215-M221.

"Absorbable Hemostatic Particles Microporous Polysaccharide Hemosphere (MPH®) Technology", medafor Hemostatic Polymer Technologies, LIT-0057 Rev E 10/08 (2 pgs.) http://www.medaforinc.com/documents/products/AristaAH.pdf , Oct. 2008.

J. Fannon, R. Hauber, J. BeMiller, "Surface Pores of Starch Granules", 1992 American Association of Cereal Chemists, Inc., vol. 69, No. 3, 1992 (5 pgs.).

"About Medafor", medafor Hemostatic Polymer Technologies, http://www.medaforinc.com/about.aspx, (3 pgs.), Printed on Oct. 3, 2011.

J. Fannon, J. Gray, N. Gunaway, K. Huber, J. BeMiller, "Heterogeneity of Starch Granules and the Effect of Granule Channelization on Starch Modification", Whistler Center for Carbohydrate Research, Purdue University, received Jun. 25, 2003/revised Nov. 28, 2003, Paper presented in Symposium on Modified Starches, American Chemical Society, New Orleans, Louisiana (8 pgs.), Mar. 23-27, 2003.

B. Lindberg, K. Lote, H. Teder, "Biodegradable Starch Microspheres—A new Medical Tool", Microspheres and Drug Therapy, Pharmaceutical, Immunological and Medical Aspects, Elsevier Science Publishers B.V. (36 pgs.), 1984.

Magle Life Sciences; Magle AB—Our Products, "Products", http://www.magle.se/our_products; jsessionid=033C6D6E207028CB7F1806B2795DBCD6 (2 pgs) Printed on Nov. 1, 2011.

Tina B. Merritt DVM, "Help! My Bird is Bleeding", Winged Wisdom Pet Bird Magazine, Ezine, Nov. 1997 Magazine, Article V, http://www.birdsnways.com/wisdom/ww17ev.htm (2 pgs) Printed on Nov. 1, 2011.

C. Tschan M. Nie, E. Schwandt, J. Oertel, "Safety and Efficacy of Microporous Polysaccharide Hemospheres in Neurosurgry", Neurosurgery . 69 Operative Neurosurgery, 1:ons49-ons63, Sep. 2011. doi: 10.1227/NEU.06-13e3182155a51 (16 pgs) printed Nov. 1, 2011 http://stage-mobile.journals.lww.com/neurosurgery/_layouts/oaks.journals.mobile/articlevi.

* cited by examiner

METHOD OF MAKING A HEMOSTATIC SPONGE WOUND DRESSING COMPRISING SUBJECTING THE SPONGE TO WATER VAPOR

CROSS REFERENCE TO RELATED APPLICATIONS

This application claims the benefit under 35 U.S.C. §119 (e) to U.S. Provisional Patent Application Ser. No. 61/068226, filed Mar. 4, 2008, entitled "Hemostatic Sponge and Method of Manufacture", which is incorporated herein by reference in its entirety.

TECHNICAL FIELD OF THE INVENTION

This disclosure relates generally to wound dressings and more particularly to a hemostatic sponge and a method of making hemostatic sponges.

BACKGROUND OF THE INVENTION

Human blood forms clots to stop bleeding from wounds. Sometimes, however, it is desirable to stop bleeding and facilitate clotting faster than the human body can achieve on its own. To clot blood more quickly, medical personnel sometimes use sponges made of hemostatic agents. These sponges may be referred to as hemostatic sponges. Some hemostatic sponges may be brittle and prone to cracking and/or may fail to adhere effectively to a wound site in some circumstances.

SUMMARY OF THE INVENTION

In one embodiment, a method of making a wound dressing comprises dissolving at least one hemostatic agent in at least one solvent to form a solution. The method continues by freeze drying the solution to form a sponge. The method further comprises compressing the sponge, wherein the sponge is subjected to a vapor above ambient temperature prior to or during the compression.

Various embodiments described herein may have none, some, or all of the following advantages. One advantage is that a wound dressing made in accordance with the invention may be more adhesive to a wound site than some existing hemostatic sponges. In some embodiments, the wound dressing comprises a sponge that is subjected to a vapor treatment and compressed during manufacture. The vapor treatment may alter the size and/or configuration of fibers and/or pores on at least one surface of the sponge. The altered fibers and/or pores may make the sponge more flexible and less prone to cracking than some existing hemostatic sponges. In some embodiments, the altered fibers and/or pores may increase the adhesiveness of the sponge to a wound, making it less likely to detach before the wound stops bleeding. In some embodiments, the vapor treatment increases the density of the sponge. A sponge with an increased density may be less likely to dissolve when applied to wounds with high pressure bleeding. In some embodiments, the hemostatic sponge comprises a chitosan material which may have antimicrobial properties that are beneficial for injury victims. Other advantages of the present invention will be readily apparent to one skilled in the art from the description and the appended claims.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION OF THE INVENTION

The preferred embodiment of the invention and its advantages are best understood by referring to FIGS. 1-5 of the drawings, like numerals being used for like and corresponding parts of the various drawings. The embodiments described herein are only example embodiments of the invention and various substitutions and alterations can be made without departing from the scope of the invention.

Figure 1:
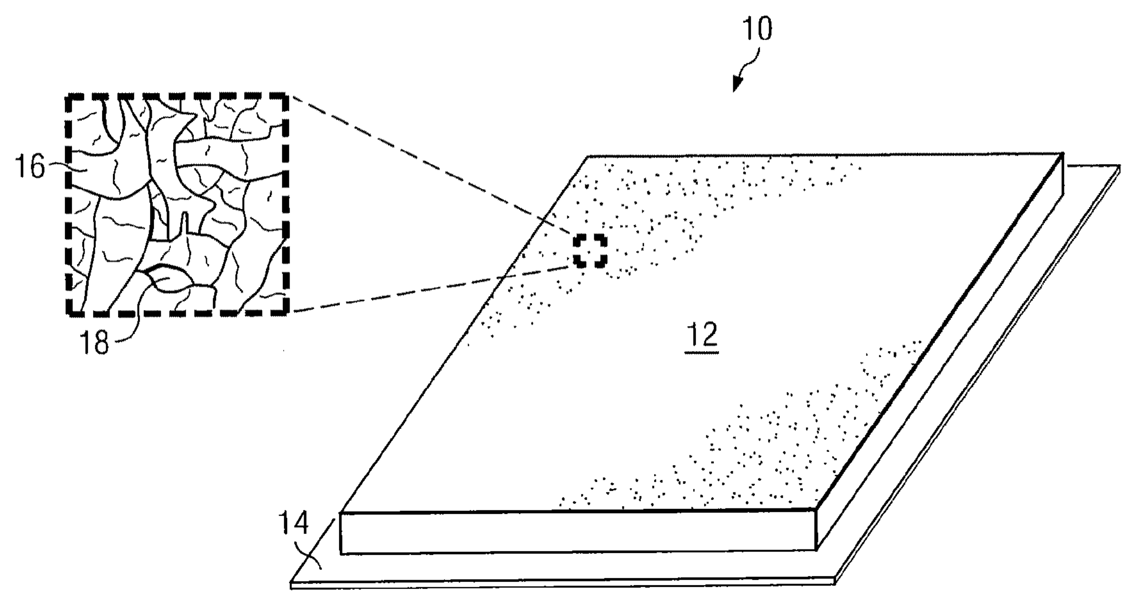
FIG. 1 illustrates a wound dressing, according to at least one embodiment of the invention.

FIG. 1 illustrates an example wound dressing 10 constructed in accordance with the teachings of the invention. Wound dressing 10 may comprise a hemostatic sponge 12 and a backing 14. Sponge 12 may be placed in contact with a bleeding wound to accelerate and/or promote clotting of blood around the wound. Sponge 12 may be used to promote clotting for blood flows that arise from trauma, medical procedures, nose bleeds, dental procedures, and/or other causes. Wound dressing 10 may be made at least in part by freeze-drying a hemostatic solution to form sponge 12. A press may then compress at least part of sponge 12. Prior to and/or during the compression process, sponge 12 may be treated with a vapor such as, for example, water vapor. This vapor treatment may increase the flexibility, adhesiveness, porosity, and/or density of sponge 12. By treating sponge 12 with a vapor during its manufacture, sponge 12 may be more adhesive to a wound site and may be more likely to clot a bleeding wound than other hemostatic sponges.

Sponge 12 may comprise at least one hemostatic agent. The hemostatic agent may be any suitable substance that promotes clotting of blood and/or halts bleeding. In some embodiments, the hemostatic agent is a polysaccharide. The polysaccharide may be a starch such as, for example, potato starch, corn starch, amylopectin, modified (cross-linked) pregelatinized amylopectin, and/or other suitable modified or unmodified starch. In some embodiments, the polysaccharide may be glycogen, chitosan, a chitosan derivative (e.g., carboxyl methyl chitosan, deacetylated chitosan, trimethylchitosan, etc.), gelatin, and/or other suitable polysaccharide. Other hemostatic agents that may be used include polycarbophils (e.g., calcium carbophil), mucoadhesive polymers, hydrocolloids, sephadex, debrisan, and/or other suitable substances. Sponge 12 may comprise a single type of hemostatic agent or a combination of multiple types of hemostatic agents.

In some embodiments, sponge 12 may further comprise a binding agent, clotting accelerator, and/or medication. A binding agent may be dissolved with the hemostatic agent in a solvent. The binding agent may bind together the polymers in the solution. A binding agent may increase or decrease the flexibility of sponge 12, the liquid holding capacity of sponge 12, and/or the rate at which sponge 12 absorbs liquid. Examples of binding agents include polyethylene glycol, glycerol, sorbitol, erythritol, propylene glycol, pentaerythritol, glycerol esters, hydroxypropylmethyl cellulose (HPMC), hydroxypropylcellulose (HPC), hydroxypropylethylcellulose (HPEC), hydroxyethylcellulose (HEC), xanthum gum, guar gum, gum Arabic, and sodium carboxylmethylcellulose (CMC). Binding agents may be soluble in water and/or other solvents. In some embodiments, sponge 12 may comprise a single binding agent or a combination of different binding agents. In other embodiments, sponge 12 may not comprise any binding agents. In such embodiments, the particles of the hemostatic agent may adhere together without a binding agent.

In some embodiments, sponge 12 may comprise a clotting accelerator to speed the clotting process. The clotting accelerator may be calcium chloride, prothrombin, vitamin K, fibrin, fibrinogen, and/or any suitable clotting accelerator. The amount of clotting accelerator added to sponge 12 may depend upon the application but it may be a smaller percentage by weight or a larger percentage by weight as compared to the hemostatic agent. Sponge 12 may comprise a single clotting accelerator or a combination of different clotting accelerators. In some embodiments, such as where the hemostatic agent is sufficient to clot blood by itself, sponge 12 may not comprise any clotting accelerators.

According to certain embodiments, sponge 12 may comprise one or more medications. Medications may include antibacterials, antifungals, antiseptics, polyglucans, and/or other suitable drugs. One or more medications may be mixed with the hemostatic agent while sponge 12 is being made or may be applied to a surface of sponge 12 after manufacture.

In some embodiments, wound dressing 10 may comprise backing 14 that is attached to at least one surface of sponge 12. Backing 14 may permit wound dressing 10 to be packaged, handled, and/or applied to a wound in a sterile and secure manner. Backing 14 may be made of cloth, plastic, paper, film, and/or any suitable material. Backing 14 may be attached to at least one surface of sponge 12 with an adhesive, stitching, staples, and/or any suitable fastener.

The process for manufacturing sponge 12 may enhance its hemostatic properties. Sponge 12 may be manufactured by freeze-drying a solution that comprises at least one hemostatic agent. The freeze-drying process may cause the solution to change from a liquid to a solid, sponge-like form. Sponge 12 may then be subjected to a vapor treatment and to a compression process. The vapor treatment may, at least in part, increase the porosity, average pore diameter, flexibility, adhesiveness, and/or density of sponge 12.

In some embodiments, a surface of a compressed sponge 12 comprises a mesh of microscopic fibers 16. Fibers 16 may be intertwined to form microscopic pores 18. The size of fibers 16 and pores 18 may affect the hemostatic properties of sponge 12. In some embodiments, the vapor treatment may enlarge the average size of fibers 16 and/or pores 18 on at least one surface of sponge 12. The enlarged fibers 16 may occupy more surface area of sponge 12 than other fibers in other hemostatic sponges. Thus, the enlarged fibers 16 in sponge 12 may increase the adhesiveness and clotting ability of sponge 12. In some embodiments, the vapor treatment may increase the density, porosity, flexibility, and/or average pore diameter of sponge 12.

Porosity may be a measurement of the void spaces in sponge 12. Porosity may be expressed according to any suitable metric. In some embodiments, porosity may be expressed as a fraction or percentage of the volume of void space in sponge 12 to the total volume of sponge 12. Porosity of sponge 12 may be measured according to any suitable technique. Such techniques may include mercury intrusion porosimetry, gas pycnometry, water evaporation, water saturation, and the volume/density method. In some embodiments, a compressed sponge 12 in wound dressing 10 may have porosity from 60.0% to 80.0% as measured by mercury intrusion. In certain embodiments, a compressed sponge 12 in wound dressing 10 may have porosity from 68.0% to 73.0% as measured by mercury intrusion. It should be understood, however, that sponge 12 may be configured to have any suitable porosity.

Sponge 12 in wound dressing 10 may have a greater average pore diameter than other hemostatic sponges. Average pore diameter may refer to the average diameter of pores 18 in sponge 12. Average pore diameter may be expressed in micrometers, millimeters, microns, and/or according to any suitable metric. Average pore diameter of sponge 12 may be measured according to any suitable technique. Such techniques may include capillary porosimetry, mercury intrusion porosimetry, sieve techniques, and imaging techniques. In some embodiments, a surface of sponge 12 in wound dressing 10 may have an average pore diameter from 20 to 50 microns. In certain embodiments, a surface of sponge 12 in wound dressing 10 may have an average pore diameter from 25 to 30 microns. It should be understood, however, that sponge 12 may be configured to have any suitable average pore diameter. The average pore diameter or other metrics may be measured based on the entire sponge 12 or based on one or more surfaces of sponge 12. In some embodiments, the average pore diameter or other metrics may be measured at the surface of sponge 12 that is to be applied to the wound (e.g., the surface opposite backing 14).

Sponge 12 in wound dressing 10 may have a greater density than other hemostatic sponges. Density may refer to the mass per unit volume of sponge 12. Density may be expressed as $kg/m^3$, $g/cm^3$, or according to any suitable metric. Density of sponge 12 may be measured according to any suitable technique. Such techniques may include direct measurement, mercury intrusion porosimetry, liquid displacement, and gas pycnometer techniques. In some embodiments, the volume and mass of sponge 12 may be measured directly to determine density. For example, for a square or rectangular sponge 12, the geometric volume of sponge 12 may be measured by multiplying the length, width, and thickness of sponge 12. The mass of sponge 12 may be measured directly using a scale or other suitable equipment. In this example, the density of sponge 12 may then be determined by dividing the determined mass by the geometric volume. In some embodiments, sponge 12 in wound dressing 10 may have a density from 0.20 to 0.40 $g/cm^3$. According to certain embodiments, sponge 12 in wound dressing 10 may have a density from 0.25 to 0.35 $g/cm^3$. It should be understood, however, that sponge 12 may have any suitable density.

Sponge 12 in wound dressing 10 may be more flexible than other hemostatic sponges. Flexibility may refer to the amount of deformation, caused by force or stress, that sponge 12 can tolerate without cracking. Flexibility may be measured according to any suitable technique. In one embodiment, a force is applied to the center of sponge 12, which is suspended on or in a brace. A force gauge may measure the force that sponge 12 tolerates before cracking. In some embodiments, sponge 12 in wound dressing 10 may exhibit flexibility from 3.75 to 8.00 ft-lb. It should be understood, however, that sponge 12 may be configured to exhibit any suitable amount of flexibility.

Sponge 12 in wound dressing 10 may be more adhesive than other hemostatic sponges. Adhesiveness may refer to the pulling or separating force that sponge 12 may tolerate before detaching from the wound site. Adhesiveness may be measured according to any suitable technique. According to one example, adhesiveness may be measured by placing wound dressing 10 in a Petri dish that is at least partially filled with water. In this example, wound dressing 10 comprises sponge 12 that is attached to a rubber backing 14. A ¼" female national pipe thread taper (NPT) fitting is attached by two sided tape to the center of the upper surface of the rubber backing 14. A nylon fiber approximately 0.007 inches in diameter (e.g., dental floss) is then wrapped around the rubber backing 14, the NPT fitting, and sponge 12 to prevent these components from separating from each other during the adhesion test.

In this example, the Petri dish is made of polystyrene and is partially filled with 500 ml of water between 40 and 44° C. The Petri dish may have dimensions of 150 by 20 mm such as, for example, part number 3488G55 supplied by Thomas Scientific. The bottom surface of sponge 12 (i.e., the surface of sponge 12 that is to be applied to a wound) is initially placed in the water in the Petri dish for approximately five seconds. In this example, the bottom surface of sponge 12 is approximately 3.75 by 3.75 inches square. Wound dressing 10 is then pressed to the bottom of the Petri dish such that the bottom surface of sponge 12 is in contact with the bottom of the inside of the Petri dish. A weight is then set on top of wound dressing 10. In this example, the weight is approximately thirty pounds and is cylindrical with a diameter of approximately five inches. Wound dressing 10 is permitted to soak in the Petri dish at room temperature for approximately two hours.

In this example, after wound dressing 10 soaks in the Petri dish for two hours, a threaded rod is screwed into the ¼" NPT fitting attached to wound dressing 10. The threaded rod is attached to a force gauge and an upward force is applied to the rod while the Petri dish is held in place. In this example, the upward force is substantially perpendicular to the bottom surface of sponge 12. The maximum upward force that is required to achieve separation of sponge 12 from the Petri dish may indicate the adhesiveness of sponge 12.

In some embodiments, the maximum force required to separate sponge 12 from the Petri dish may be divided by the surface area of the bottom of sponge 12 to calculate the adhesiveness of sponge 12 per unit of surface area. In some embodiments, it would be desirable for sponge 12 to exhibit adhesiveness from 2.20 to 5.00 ft-lb/in$^2$ when tested according to the above technique. In other embodiments, it would be desirable for sponge 12 to exhibit adhesiveness from 2.50 to 5.00 ft-lb/in$^2$ when tested according to the above technique. According to certain embodiments, it would be desirable for sponge 12 to exhibit adhesiveness from 2.85 to 5.00 ft-lb/in$^2$ when tested according to the above technique. In some embodiments, it would be desirable for sponge 12 to exhibit adhesiveness from 3.00 to 5.00 ft-lb/in$^2$ when tested according to the above technique. According to certain embodiments, it would be desirable for sponge 12 to exhibit adhesiveness from 3.25 to 5.00 ft-lb/in$^2$ when tested according to the above technique. In some embodiments, it would be desirable for sponge 12 to exhibit adhesiveness from 2.20 to 4.50 ft-lb/in$^2$ when tested according to the above technique. In other embodiments, it would be desirable for sponge 12 to exhibit adhesiveness from 2.50 to 4.50 ft-lb/in$^2$ when tested according to the above technique. According to certain embodiments, it would be desirable for sponge 12 to exhibit adhesiveness from 2.85 to 4.50 ft-lb/in$^2$ when tested according to the above technique. In some embodiments, it would be desirable for sponge 12 to exhibit adhesiveness from 3.00 to 4.50 ft-lb/in$^2$ when tested according to the above technique. According to certain embodiments, it would be desirable for sponge 12 to exhibit adhesiveness from 3.25 to 4.50 ft-lb/in$^2$ when tested according to the above technique. In some embodiments, it would be desirable for sponge 12 to exhibit adhesiveness from 2.20 to 4.00 ft-lb/in$^2$ when tested according to the above technique. In other embodiments, it would be desirable for sponge 12 to exhibit adhesiveness from 2.50 to 4.00 ft-lb/in$^2$ when tested according to the above technique. According to certain embodiments, it would be desirable for sponge 12 to exhibit adhesiveness from 2.85 to 4.00 ft-lb/in$^2$ when tested according to the above technique. In some embodiments, it would be desirable for sponge 12 to exhibit adhesiveness from 3.00 to 4.00 ft-lb/in$^2$ when tested according to the above technique. According to certain embodiments, it would be desirable for sponge 12 to exhibit adhesiveness from 3.25 to 4.00 ft-lb/in$^2$ when tested according to the above technique.

Although the foregoing example describes particular ranges of adhesiveness, it should be understood that sponge 12 may be configured to exhibit any suitable amount of adhesiveness.

As stated above, the vapor treatment of sponge 12 may enlarge the average size of fibers 16 in sponge 12. The enlarged fibers 16 may occupy more surface area of sponge 12 than other fibers in other hemostatic sponges. These enlarged fibers 16 may permit sponge 12 to be more compact while providing at least the same absorptive capabilities as other hemostatic sponges. In some embodiments, sponge 12 may be from three inches to five inches square and less than 0.20 inches thick. Thus, sponge 12 may be thinner than other hemostatic sponges. Even where sponge 12 in wound dressing 10 is less than 0.20 inches thick, sponge 12 may be at least as absorptive as other hemostatic sponges. In some embodiments, the enlarged fibers 16 in sponge 12 may increase the absorption properties of sponge 12. The ability of sponge 12 to absorb substances may be quantified based at least in part on the surface area of fibers 16 in sponge 12. According to the BET (Brunauer-Emmett-Teller) rule, sponge 12 may have a BET surface area that is greater than 0.50 m$^2$/g. In some embodiments, sponge 12 may have a BET surface area from 0.65 to 1.00 m$^2$/g. Thus, sponge 12 may be more compact while providing at least the same absorptive capabilities as other hemostatic sponges.

Figure 2:
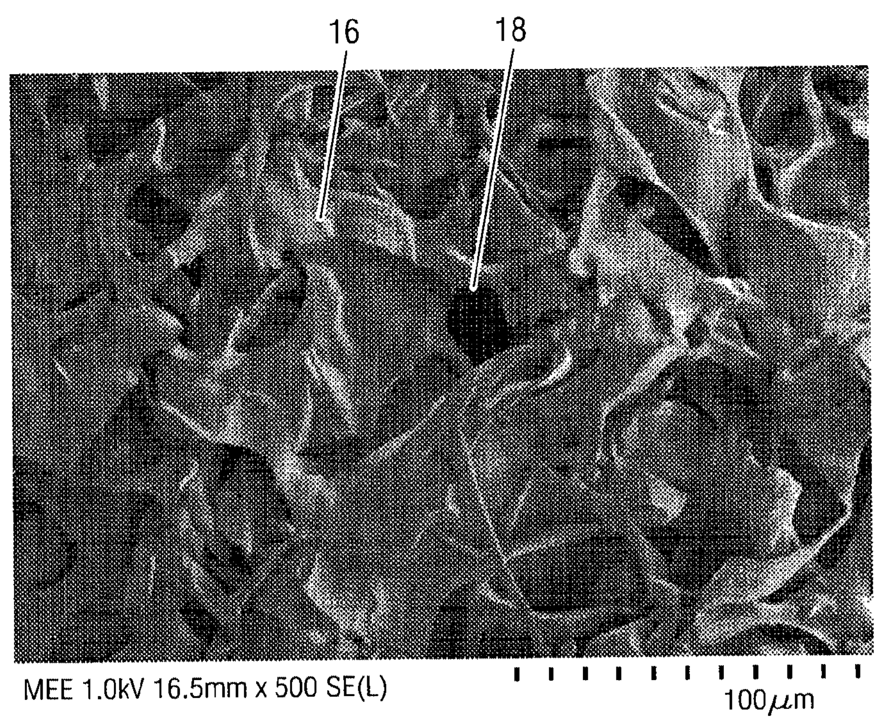
FIG. 2 is a magnified image of part of an example sponge made in accordance with one aspect of the invention.

FIG. 2 is a magnified image from a scanning electron microscope of an example sponge 12 made in accordance with the teachings of the invention. Sponge 12 comprises a plurality of intertwined fibers 16. Fibers 16 in sponge 12 may comprise at least one hemostatic agent. Fibers 16 may be arranged in a uniform or non-uniform mesh that forms a plurality of pores 18 in sponge 12. Fibers 16 and pores 18 in sponge 12 may attract and/or absorb blood cells at a wound site. In some embodiments, fibers 16 may comprise a hemostatic agent that is positively charged (e.g., chitosan), which may attract negatively charged red blood cells. As red blood cells are drawn to sponge 12, the red blood cells may form a coherent seal over the wound. Sponge 12 may thus accelerate formation of a blood clot, according to certain embodiments.

In the example image, a surface of sponge 12 is magnified 500 times. Fibers 16 and pores 18 in sponge 12 may be larger than fibers and pores in other sponges due, at least in part, to treating sponge 12 with a vapor during the manufacturing process. Although the example image shows fibers 16 of particular sizes in a particular arrangement, it should be understood that fibers 16 and pores 18 in sponge 12 may be any suitable size and arranged in any suitable uniform or non-uniform fashion. In some embodiments, the surface depicted in FIG. 2 may be the surface of sponge 12 that is to be applied to the wound site.

In operation, sponge 12 may be applied to a wound site to clot blood and/or absorb wound exudates. As sponge 12 contacts the wound site, sponge 12 may adhere to the skin or other tissues at the wound site. In some embodiments, sponge 12 may be used to control or stop bleeding in humans or animals following a traumatic injury and/or during a dental, surgical, or other medical procedure.

Figure 3:
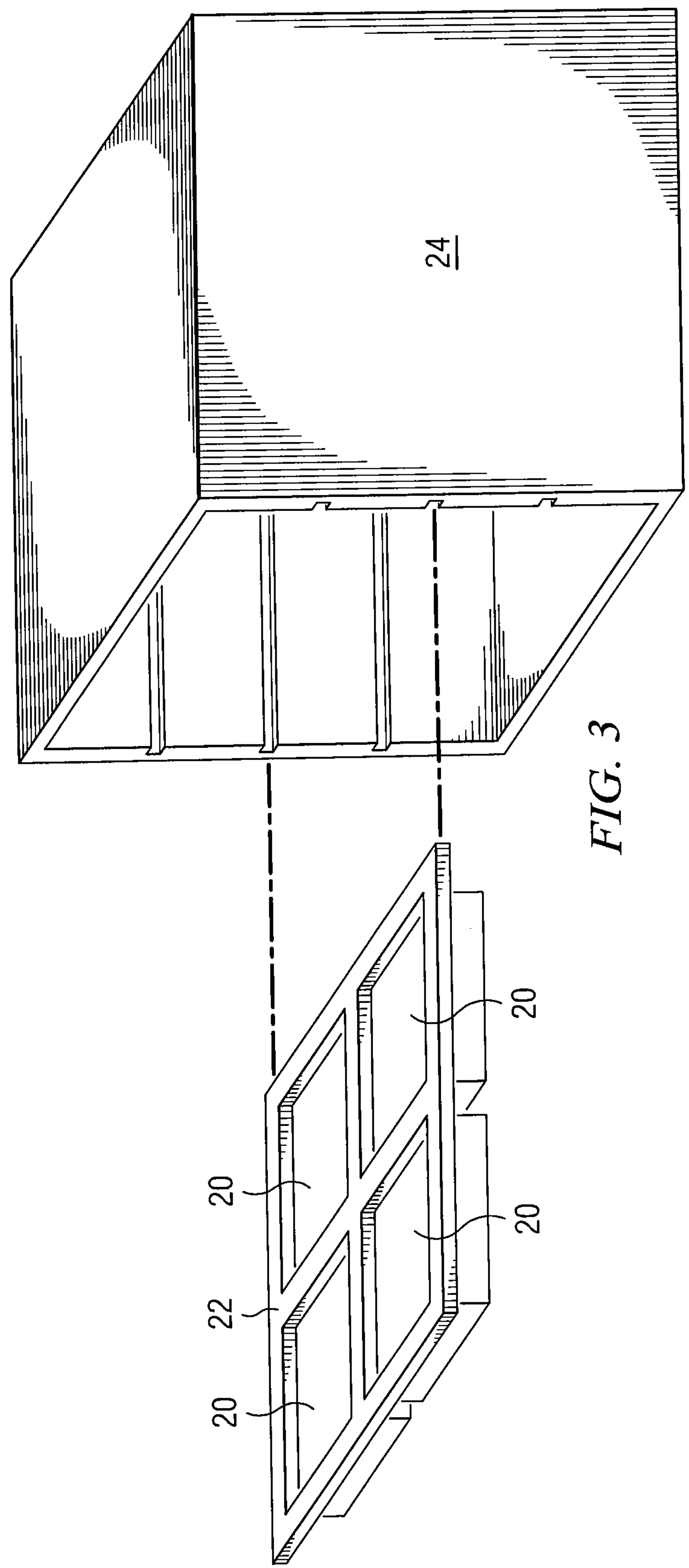
FIG. 3 illustrates the freeze-drying of a hemostatic solution to make a sponge in accordance with one aspect of the invention.
Figure 4:
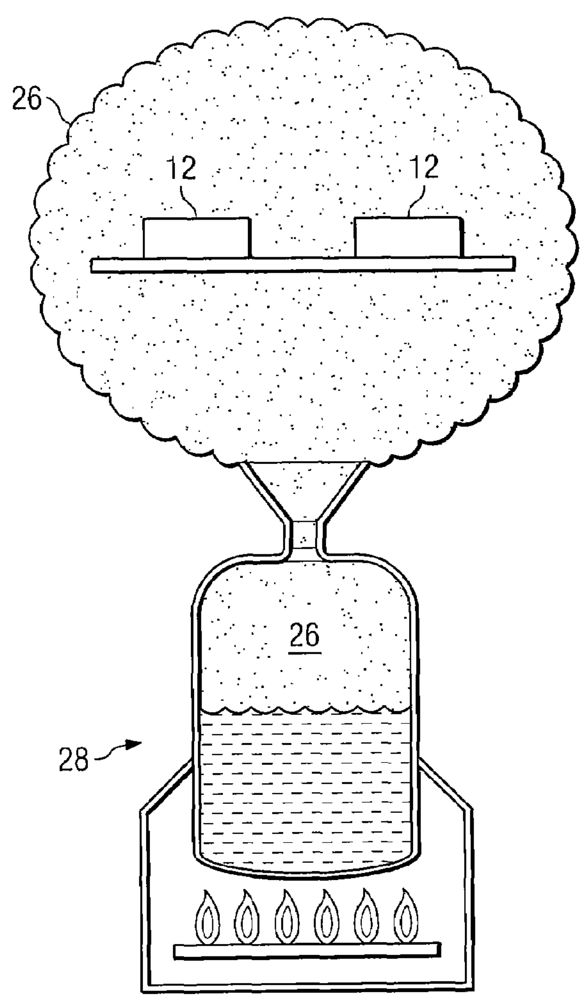
FIG. 4 illustrates a vapor treatment of a sponge in accordance with one aspect of the invention.
Figure 5:
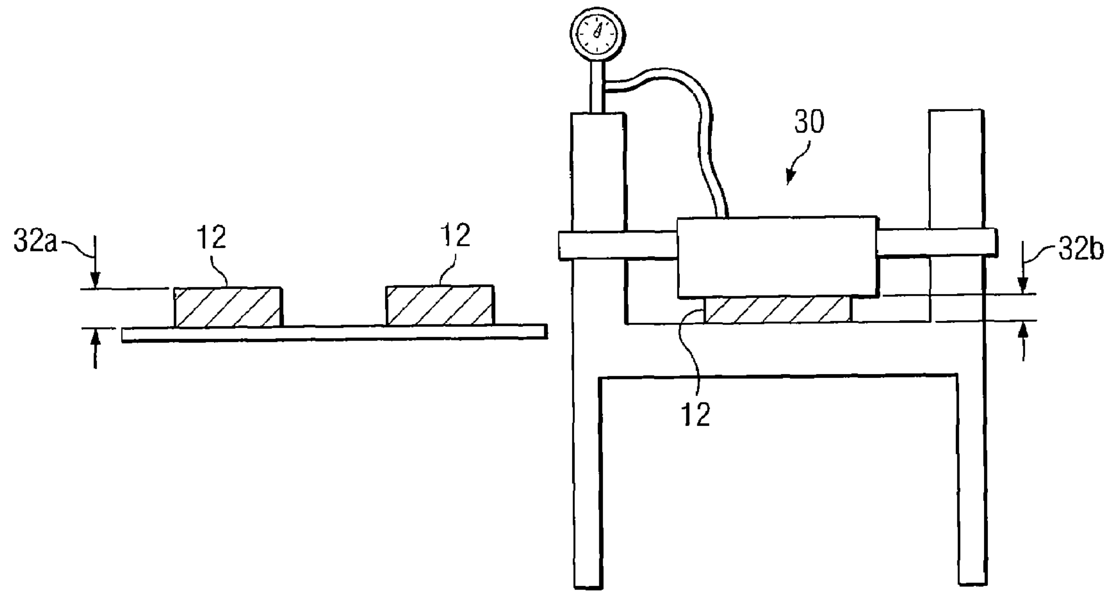
FIG. 5 illustrates the compression of a sponge in accordance with one aspect of the invention.

FIGS. 3-5 illustrate example steps for making sponge 12 in accordance with the invention. In some embodiments, the process begins by mixing at least one hemostatic agent with at least one solvent. Any suitable hemostatic agent and solvent may be mixed to make hemostatic solution 20. The solvent may be organic, non-organic, polar, non-polar, protic, and/or non-protic. In some embodiments, the solvent may be a polar protic solvent such as, for example, water, acetic acid, formic acid, n-Butanol, n-Propanol, isopropanol (IPA), ethanol, and/or methanol. In other embodiments, the solvent may be a polar aprotic solvent such as, for example, dimethylformamide (DMF), 1,4-Dioxane, acetonitrile (MeCN), or tetrahydrofuran (THF). In yet other embodiments, the solvent may be a non-polar solvent such as, for example, toluene, benzene, or ethyl acetate.

The hemostatic agent(s) and solvent(s) may be mixed according to any suitable ratio to make hemostatic solution 20. The percent by weight of hemostatic agent(s) may be greater or less than the percent by weight of solvent(s) in hemostatic solution 20. In some embodiments, one or more hemostatic agents may be dissolved in one or more solvents. For example, chitosan may be mixed with acetic acid and water to form hemostatic solution 20. In this example, hemostatic solution 20 may be two percent by weight of chitosan and two percent by weight of acetic acid dissolved in water. It should be understood, however, that any suitable ratios of hemostatic agents and solvents may be used.

In some embodiments, after hemostatic solution 20 is mixed, it may be sheared such as, for example, by shearing in a blender. Shearing may promote consistent mixing and may produce a more consistent sponge 12. Hemostatic solution 20 may then be degassed to remove any bubbles that are present. The shearing and/or degassing process may be omitted in some embodiments.

Hemostatic solution 20 may then be poured into one or more molds 22 and placed in a freeze-dryer 24. FIG. 3 illustrates the freeze-drying of hemostatic solution 20 in mold 22. Mold 22 may be a hollow form or cast that allows hemostatic solution 20 to solidify into a particular solid form. Mold 22 may be made of steel, aluminum, plastic, and/or any suitable material. In some embodiments, mold 22 is coated with teflon or other suitable coating. Mold 22 may be any suitable shape and/or size. In some embodiments, mold 22 may be a hollow form that casts sponges 12 that are from three inches to five inches square and from one-half to one inch thick. It should be understood, however, that any suitable mold 22 may be used to cast sponges 12 of any suitable shape and size. In some embodiments, multiple molds 22 may be part of a single tray.

In some embodiments, mold 22 containing hemostatic solution 20 may be placed in freeze-dryer 24. Freeze-dryer 24 is generally operable to freeze hemostatic solution 20 into a solid material and to sublime frozen water from the solid material. The freeze-drying process may be referred to a lyophilization. Freeze-dryer 24 may operate at any suitable temperature to freeze hemostatic solution 20. In some embodiments, freeze-dryer 24 may be set in the range of −35° C. to −80° C. The freezing phase in freeze-dryer 24 may last for any suitable period of time. In some embodiments, freeze-dryer 24 may cool hemostatic solution 20 until it is solid. According to certain embodiments, freeze-dryer 24 may cool hemostatic solution 20 at least until hemostatic solution 20 is below its eutectic point or critical point.

Once hemostatic solution 20 is frozen, freeze-dryer 24 may initiate a drying phase. During the drying phase, the pressure in freeze-dryer 24 may be lowered and the temperature in freeze-dryer 24 may be increased such that water sublimates from the frozen hemostatic solution 20. Through the combination of the freezing and drying processes, hemostatic solution 20 may become sponge 12. In some embodiments, the amount of heat added to the chamber of freeze-dryer 24 during the drying phase may be based at least in part on the latent heat of sublimation of molecules in frozen hemostatic solution 20. The chamber of freeze-drier may be maintained at any suitable temperature. In some embodiments, the temperature in the chamber may be maintained below the melt-back temperature of hemostatic solution 20.

The pressure in freeze-dryer 24 may be maintained at any suitable level during the drying phase. In some embodiments, the pressure in freeze-dryer 24 may be maintained at a vacuum or partial vacuum level. The drying phase may last for any suitable period of time. According to certain embodiments, the drying phase may last from 40 to 60 hours. In some embodiments, the drying phase may last until a configurable percentage (e.g., 90%, 95%, etc.) of the water in sponge 12 is sublimated. Freeze-dryer 24 may comprise a temperature probe that monitors the temperature of sponge 12. In some embodiments, sponge 12 may be considered sufficiently dry when the temperature of sponge 12 equals or exceeds the shelf temperature in freeze-dryer 24. Although FIG. 3 illustrates a particular freeze-dryer 24 that performs the freezing and drying in the same chamber, it should be understood that the freezing and drying may be performed in different chambers. Any suitable type and combination of equipment may be used to freeze and dry hemostatic solution 20. In some embodiments, a manifold freeze-dryer and/or tray freeze-dryer may be used.

In some embodiments, once sponge 12 is dried, it is removed from mold 22 and subjected to a vapor 26. FIG. 4 illustrates a vapor treatment of sponge 12, according to certain embodiments. Vapor 26 may refer to the state of a substance that exists below its critical temperature and that may be liquefied by application of sufficient pressure. Any suitable vapor 26 may be applied to sponge 12. In some embodiments, vapor 26 may be water vapor 26. In other embodiments, vapor 26 may be from acetone, vinegar, benzene, carbon tetrachloride, methyl alcohol, trichloroethylene, and/or other suitable type or combination of substances. Vapor 26 may be applied to sponge 12 according to any suitable technique. In some embodiments, vaporizer 28 may be used to produce and apply vapor 26 to sponge 12. Vaporizer 28 may comprise a heat source, a tank comprising a liquid bath, and a duct. Heat source may heat the liquid (e.g., water, carbon tetrachloride, or other suitable liquid) in the tank to a configurable temperature, causing the liquid in the tank to vaporize. Vapor 26 may then flow through a duct to sponge 12. Although particular components of vaporizer 28 are illustrated, any suitable type and combination of equipment may be used to generate and/or apply vapor 26 to sponge 12. For example, a boiler, direct-fired vaporizer, electric vaporizer, adiabatic humidifier, isothermic humidifier, ultrasonic humidifier, water bath vaporizer, and/or any suitable equipment may be used.

Vapor 26 may be at any suitable temperature when it is applied to sponge 12. In some embodiments, vapor 26 is above ambient temperature when it is applied to sponge 12. Ambient temperature may refer to the temperature of the room, building, or space in which sponge 12 is manufactured. In a preferred embodiment, vapor 26 is between 50° C and 70° C. Sponge 12 may be exposed to vapor 26 for any suitable period of time. In some embodiments, sponge 12 is exposed to vapor 26 for 30 to 120 seconds.

After and/or during the vapor treatment, sponge 12 may be compressed. FIG. 5 illustrates the compression of sponge 12, according to certain embodiments. Sponge 12 may be placed in a press 30. Press 30 may be any suitable device that applies pressure to sponge 12. In some embodiments, press 30 comprises two or more plates between which sponge 12 is positioned. As the plates are forced toward each other, sponge 12 may be compressed such that its thickness 32 is reduced in at least one dimension. In other embodiments, press 30 may comprise rollers. As sponge 12 is forced through the rollers of press 30, sponge 12 may be compressed such that it becomes thinner in at least one dimension. Any suitable type of compression equipment may be used. For example, press 30 may be a hydraulic press, manual press, pneumatic press, roller press, stamping machine, or servo press.

Press 30 may compress sponge 12 until a desired thickness 32 in at least one dimension is achieved. In some embodiments, sponge 12 has an original thickness 32*a* prior to being compressed. The original thickness 32*a* may correspond to the depth of mold 22 used during the freezing process. For example, prior to being compressed, sponge 12 may have dimensions of 4.0 inches by 4.0 inches by 0.8 inches. In this example, the original thickness 32*a* of sponge 12 is 0.8 inches. In some embodiments, press 30 may be configured to compress sponge 12 to reduce its thickness 32*b* to any suitable fraction (e.g., one-fourth, one-eighth, one-tenth, etc.) of the original thickness 32*a*. For example, for sponge 12 with an original thickness 32*a* of 0.8 inches, press 30 may be configured to compress sponge 12 until its thickness 32*b* is reduced to 0.1 inches. Although the foregoing example describes particular dimensions and compression ratios, it should be understood that sponge 12 may have any suitable dimensions and may be compressed according to any suitable compression ratio.

In some embodiments, press 30 may apply any suitable amount of force for any suitable length of time to compress sponge 12. In some embodiments, press 30 compresses sponge 12 for twenty to sixty seconds. According to certain embodiments, press 30 compresses sponge 12 with a pressure from 110 psi to 3,000 psi. In some embodiments, press 30 compresses sponge 12 at a rate from fifteen to thirty mm/minute. It should be understood, however, that sponge 12 may be compressed for any suitable length of time, at any suitable rate, and with any suitable amount of pressure.

The compression of sponge 12 may be done at any suitable temperature. In some embodiments, sponge 12 is compressed at ambient temperature. In other embodiments, press 30 may be configured to add heat to sponge 12 while it is being compressed. For example, press 30 may have plates, rollers, and/or die that are heated while in contact with sponge 12. In some embodiments, sponge 12 may be compressed at a temperature that is below ambient temperature. For example, press 30 may be associated with a compressor, cooling coils, and/or other suitable refrigeration equipment that cools sponge 12 while it is being compressed.

In some embodiments, the compression of sponge 12 contributes to altering the structure of fibers 16 in and/or the porosity of sponge 12. The combination of the vapor treatment and the compression of sponge 12 may enlarge the surface area of fibers 16 on at least one surface of sponge 12. With an enlarged surface area, these fibers 16 may attract red blood cells more strongly than fibers in other hemostatic sponges. In some embodiments, the enlarged surface area of fibers 16 may increase the adhesiveness of sponge 12 to a wound.

FIGS. 4 and 5 illustrate the vapor treatment of sponge 12 occurring separately from the compression of sponge 12. In some embodiments, however, the vapor treatment may occur while sponge 12 is being compressed. For example, vaporizer 28 may be associated with press 30 such that vapor 26 is applied to sponge 12 while press 30 is compressing sponge 12. In some embodiments, press 30 may comprise a perforated plate, roller, or die. A duct, tube, pipe, or other suitable vapor conduit may couple the perforated plate, roller, or die to vaporizer 28. Thus, while sponge 12 is being compressed, vapor 26 from vaporizer 28 may flow through the perforated plate, roller, or die of press 30 to at least one surface of sponge 12. Without departing from the scope of this disclosure, any other suitable type and/or configuration of equipment may be used to apply vapor 26 to sponge 12 during the compression process.

The present disclosure encompasses all changes, substitutions, variations, alterations, and modifications to the example embodiments described herein that a person having ordinary skill in the art would comprehend. Similarly, where appropriate, the appended claims encompass all changes, substitutions, variations, alterations, and modifications to the example embodiments described herein that a person having ordinary skill in the art would comprehend.

To aid the Patent Office and any readers of any patent issued on this application and interpreting the claims appended hereto, Applicants wish to note that they do not intend any of the appended claims to invoke Paragraph 6 of 35 U.S.C. §112 as it exists on the date of filing hereof unless "means for" or "step for" are used in the particular claim.

What is claimed is:

1. A method of making a wound dressing, comprising:

dissolving at least one of chitosan, carboxyl methyl chitosan, deacetylated chitosan, or trimethylchitosan in at least one aqueous solvent to form a solution;

freeze drying the solution to form a sponge; and compressing the sponge to form a compressed sponge, wherein the sponge is intentionally subjected to water vapor from a vaporizer for 30 to 120 seconds prior to the compression, the water vapor being between 50° C. and 80° C.

2. The method of claim 1, wherein:

the at least one aqueous solvent comprises acetic acid.

3. The method of claim 1, wherein freeze drying the solution to form a sponge comprises:

freezing the solution in a mold at a temperature between −35 and −80° C., wherein the solution becomes a solid material; and sublimating water from the solid material.

4. The method of claim 1, wherein the vaporizer is selected from the group consisting of: a boiler, a direct-fired vaporizer, an electric vaporizer, an adiabatic humidifier, an isothermic humidifier, an ultrasonic humidifier, and a water bath vaporizer.

5. The method of claim 1, wherein the sponge is compressed at a pressure between 120 to 3,000 psi for 20 to 120 seconds.

6. The method of claim 1, wherein:

the sponge has a first thickness prior to the compression;

the sponge is compressed until it has a second thickness; and the second thickness is one-fourth to one-sixteenth of the first thickness.

7. The method of claim 1, wherein the compressed sponge has a porosity of 60 to 80 percent as measured by mercury intrusion.

8. The method of claim 1, wherein the compressed sponge has an average pore diameter of 25 to 30 microns.

9. The method of claim 1, wherein the compressed sponge has a density of 0.20 $g/cm^3$ to 0.40 $g/cm^3$.

10. The method of claim 1, wherein the compressed sponge: is less than 0.20 inches thick; and has a BET surface area greater than 0.50 $m^2/g$.

11. The method of claim 10, wherein the compressed sponge has a porosity greater than 60 percent as measured by mercury intrusion.

12. The method of claim 1, wherein the compressed sponge exhibits adhesiveness from 2.85 to 5.00 $ft.lb/in^2$.

13. A method of making a wound dressing, comprising:

dissolving at least one of chitosan, carboxyl methyl chitosan, deacetylated chitosan, or trimethylchitosan in at least one aqueous solvent to form a solution;

freeze drying the solution to form a sponge; and compressing the sponge, wherein the sponge is intentionally subjected to water vapor for 30 to 120 seconds prior to the compression, the water vapor being between 50° C. and 80° C., and is additionally subjected to said water vapor during the compression.

* * * * *